United States Patent [19]

Marten

[11] Patent Number: 4,643,718

[45] Date of Patent: Feb. 17, 1987

[54] THERAPEUTIC APHERESIS

[75] Inventor: James F. Marten, Cohasset, Mass.

[73] Assignee: Applied Immunesciences, Inc., Menlo Park, Calif.

[21] Appl. No.: 758,065

[22] Filed: Jul. 23, 1985

Related U.S. Application Data

[63] Continuation of Ser. No. 468,158, Feb. 22, 1983, Pat. No. 4,540,401.

[51] Int. Cl.⁴ .............................................. A61M 3/00
[52] U.S. Cl. ..................................................... 604/28
[58] Field of Search ........................................ 604/4–6, 604/28; 436/829, 536, 538, 541

[56] References Cited

U.S. PATENT DOCUMENTS

| | | | |
|---|---|---|---|
| Re. 31,688 | 9/1984 | Popovich et al. | 604/6 |
| 3,850,578 | 11/1974 | McConnell | 436/829 |
| 3,887,698 | 6/1975 | McConnell et al. | 436/537 |
| 4,244,816 | 1/1981 | Vogler et al. | 604/4 |
| 4,362,155 | 12/1982 | Skurkovich | 604/28 |
| 4,428,744 | 1/1984 | Edelson | 604/6 |
| 4,429,008 | 1/1984 | Martin et al. | 436/829 |
| 4,464,165 | 8/1984 | Pollard, Jr. | 604/5 |
| 4,540,401 | 9/1985 | Marten | 604/28 |
| 4,564,599 | 1/1986 | Tanoff et al. | 436/829 |

FOREIGN PATENT DOCUMENTS

| | | | |
|---|---|---|---|
| 0082345 | 6/1983 | European Pat. Off. | 604/5 |
| 0109531 | 10/1983 | European Pat. Off. | 604/5 |
| 0111696 | 6/1984 | European Pat. Off. | 604/5 |

Primary Examiner—John D. Yasko
Attorney, Agent, or Firm—Richard L. Neeley

[57] ABSTRACT

Disclosure is made of a means and method for removing immunologically reactive compounds from the blood of living mammals. The method of the invention comprises reacting the compound with an immunological homolog of the compound, bound to the surface of a lipid vesicle and thereafter separating the resulting complex from the blood plasma of the mammal.

7 Claims, 1 Drawing Figure

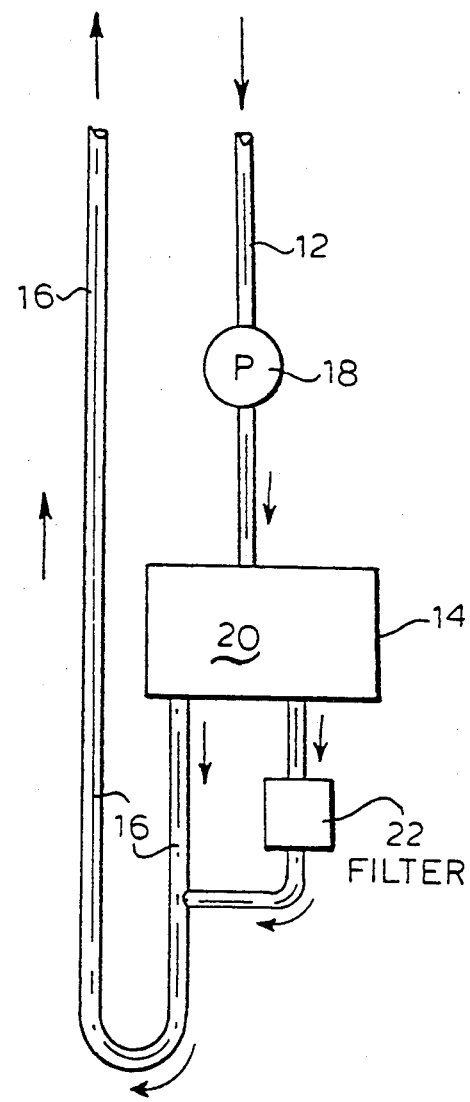

THERAPEUTIC APHERESIS

This application is a continuation, of application Ser. No. 468,158, filed Feb. 22, 1983, now U.S. Pat. No. 4,540,401.

BACKGROUND OF THE INVENTION

1. Field of the Invention

The invention relates to methods of purifying the blood of a living mammal and more particularly relates to therapeutic apheresis.

2. Brief Description of the Prior Art

Therapeutic apheresis is a medical procedure for removing specific entities from the blood of a living mammal and circulating the treated blood in the mammal. Representative of entities which may be removed are blood serum factors, antigens, antibodies, immune complexes and the like.

Plasmapheresis is an apheretic technique whereby whole blood is withdrawn from the mammal in an extracorporeal circuit and separated into its plasma and non-plasma components. In early procedures, the plasma component was discarded and the non-plasma component returned to circulation in the mammal; see for example U.S. Pat. No. 4,086,924. In later procedures, the plasma component was subjected to purification steps and also returned to circulation in the mammal's body; see for example U.S. Pat. Nos. 4,223,672 and 4,243,532.

The currently available procedures for therapeutic apheresis are fairly sophisticated, requiring highly trained personnel and complicated apparatus. The cost for a single treatment may be as much as a thousand dollars or more. There is therefore a need for an improved procedure which is simpler and less costly to carry out. The method of the present invention is such an improvement, as it relates to the removal of undesirable immunologically reactive blood components from the blood of a living mammal. The method of the invention also improves the safety factors in therapeutic apheresis.

SUMMARY OF THE INVENTION

The invention comprises a method of removing an immunologically reactive compound from the blood of a living mammal, which comprises;
reacting the compound with an immunological homolog bound to the surface of a lipid vesicle; and
separating the resulting complex from the blood plasma.

The term "immunologically reactive" is used herein to refer to that class of chemistry known as "immunochemistry". Immunochemistry is chemistry classically concerned with the physical interaction between "antigens" and "antibodies".

Antigens and antibodies are representative of "immunologically reactive compounds". Also within the scope of the latter term are haptens, which are "incomplete" antigens incapable themselves of provoking an immune response but when bound to an antigenic material will provoke formation of antibodies which will recognize the hapten molecule.

"Antigens" are high molecular weight compounds (circa 10,000 Daltons), usually protein or protein-polysaccharide complexes, which upon entry in the blood stream of a vertebrate stimulate the transformation of the small lymphocytes of the B-type into lymphoblasts. The lymphoblasts synthesize and secrete "antibodies" specific to the antigen stimulator. The antibodies are proteins (molecular weight circa 160,000–1,000,000) possessing reactive sites specifically complimentary to a reactive feature or site on the stimulating antigen. Antibodies generally have the property of rendering the antigen harmless to the host organism, by occupying the immunologically active sites on the antigen molecules, and sometimes also by forcing precipitation or agglutination of the antigen, or by other protective mechanisms.

In some but not all applications it becomes difficult or meaningless to maintain the classical distinction between antigen and antibody, because in many regards the relation between antigen and antibody is reciprocal and each neutralizer precipitates or agglutinates the other. The basis for the distinction resides in the history of the particular substance, and this can become irrelevant outside the original antibody-generating organism. For example, immunoglobulins such as IgA, IgG, IgM, IgD and IgE are by the above definitions antibodies (actually a class of antibodies) since they are produced by plasma cells of the lymphoid system in response to the presence of an antigen (usually a multiplicity of antigens). However, the immunoglobulins can also be antigenic in behavior and responsible for the production of the specific antibodies known as anti-IgA, anti-IgG, anti-IgM, anti-IgD and anti-IgE, respectively. For this reason the antigen-antibody relationship may be advantageously described in this reciprocal way: an antibody is the "immunological-homologue" of the antigen which produced it and vice versa. An antibody and its corresponding antigen are thus homologues of each other. They may also be said to be homologous to each other.

The term "lipid vesicle" as used throughout the specification and claims means a man-made (synthetic) liposome.

BRIEF DESCRIPTION OF THE DRAWING

The accompanying drawing is a schematic block drawing of a system for carrying out an embodiment method of the invention.

DETAILED DESCRIPTION OF THE PREFERRED EMBODIMENTS OF THE INVENTION

By the method of the invention, an immunologically reactive compound is removed from the blood of a living mammal by reacting the compound with its immunological homolog, the latter being bound to the surface of a lipid vesicle, and separating the resulting chemical complex from the blood.

Lipid vesicles (synthetic liposomes) have been known for a number of years as convenient carriers of encapsulated water soluble materials. Several methods are available to make lipid vesicles, encapsulating water-soluble materials; see for example Bangham et al. in J. Mol. Biol., 13:238–252 (1965); D. Papahadjopoulos and N. Miller (Biochim. Biophys. Acta, 135:624–638 [1967]; Batzri and Korn (Biochim. Biophys. Acta, 2981015 [1973]; Deamer and Bangham in Biochim. Biophys. Acta, 443:629–634 [1976]; Papahadjopoulos et al. in Biochim. Biophys. Acta, 394:483491 [1975]; German Pat. No. 2,532,317; and U.S. Pat. Nos. 3,804,776; 4,016,100 and 4,235,871.

Lipid vesicle wall forming compounds are generally well known as are the methods of their preparation. For example, any number of phospholipids or lipid compounds may be used to form the vesicle walls. Representative of such wall forming compounds are those described in the U.S. Pat. No. 4,235,871, the disclosure of which is hereby incorporated herein by reference thereto.

The lipid vesicles employed in the present invention are prepared, encapsulating inert compositions, i.e.; compositions which will not adversely affect the desired course of the therapeutic apheresis in which they are employed in the method of the invention. Representative of inert compositions encapsulated in the lipid vesicles used in the method of the invention are saline, buffer solutions and the like. In one embodiment of the invention, the inert compositions may include tracers for locating and identifying the containing lipid vesicle during their free circulation during practice of the method of the invention. Representative of tracers which may be in the encapsulated compositions are chromogens which both absorb and emit light, i.e.; fluorescers. Representative of fluorescers are: 3,6-dihydroxy-9-phenylxanthydrol, 2-amino-6-sulfonatonaphthalene, bis(3'-aminopyridinium) and the like. A preferred class of fluorescer is a member of the group consisting of an N-substituted benzamide represented by the formula:

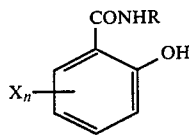

wherein R is a member of the group consisting of hydrogen and methyl, X is a member of the group consisting of halogen and alkoxy having no more than two carbon atoms, and n is an integer having a value of 0 or 1, and physiologically acceptable (tolerable) alkali metal salts thereof.

To prepare the immunochemical reagents used in the method of the invention, immunological homologs of the immunologically reactive compounds desired to be removed from the mammal's blood are bound to the membrane surface of the lipid vesicle, encapsulating the inert composition.

For example, if the species to be removed from the mammal's blood is an antigen, then the immunochemical reagent for its removal comprises a lipid vesicle having bound to its surface the appropriate antibody counterpart of the antigen. If the undesired species is an antibody, then the corresponding or homolog antigen bound to the lipid vesicle is used as the immunochemical reagent. The binding of the antigen or antibody to the surface of the lipid vesicle may be chemical to produce a "sensitized" lipid vesicle or reagent vesicle. The term "chemically bound" as used herein means a binding caused by the interaction of individual atoms. Chemical bonding comprises, for example, covalent bonding, hydrogen bonding, hydrophobic bonding, intercalation and the like.

Methods of binding antigens to the surface of lipid vesicles are well known and details need not be recited herein; see for example the method described in U.S. Pat. No. 3,887,698.

Until recently, techniques for bonding antibodies to the surface of lipid vesicles were crude and only minimal densities of attachment were achieved. With newly developed techniques the antibody may be directly bound to the lipid membrane surface of the lipid vesicle or, depending on the composition of the lipid membrane, may be linked through a modified membrane surface. For example, a convenient means of binding is by first oxidizing the carbohydrate portion of the lipid vesicle membrane to convert alcohol groups to aldehyde groups, such as by exposure to sodium metaperiodate. The resulting aldehyde groups will couple antibody to the membrane surface, following the method of Fiddler and Gray, Analyt. Biochem., 86, 716–724 [1978].

Modification of the membrane surfaces will, of course, depend upon the lipid composition of the membranes. When, for example, a galactose lipid is present, oxidation of the group at the C-6 position will provide a reactive group which will covalently bond an antibody.

Antibody can also be bound to the vesicle surface through a binding molecule, such as an intermediary protein which will recognize and bind to the Fc region on the antibody. Representative of such a protein is the bacterial Protein A. Protein A has amino acid side chains which will attach to the lipid vesicle membrane following the general procedure of Fiddler and Gray, supra.

When the immunochemical reagent employed in the method of the invention comprises an antibody bound to the surface of a lipid vesicle, it is preferred that the antibody be selected from very pure forms of antibodies, to assure their high degree of sensitivity to specific antigens. This high degree of specificity is a distinct advantage in use of the reagents in the method of the invention. Advantageously, the antibody is provided in a purified form such as is obtainable by monoclonal production techniques. Such techniques are well known; see for example U.S. Pat. No. 4,196,265. Monoclonal antibodies are highly specific in their binding characteristics, affinity and uniformity and when bound to the surface of a lipid vesicle, remain as a polyclonal antibody or a monoclonal antibody possessive of an active epitopic site which is capable of immunochemical reaction with its immunological homolog.

By the method of the invention, a wide variety of immunochemicals may be removed from the blood of a living mammal. Representative proteins removable by the method of the invention are a wide variety of:

protamines,
histones,
albumins,
globulins,
scleroproteins,
phosphoproteins,
mucoproteins,
chromoproteins,
lipoproteins,
nucleoproteins,
glycoproteins and the like.

Representative of specific polypeptide and protein hormones advantageously removed by the method of the invention are:

parathyroid hormone (parathromone),
thyrocalcitonin,
insulin,
glucagen,
relaxin,
erythroporetin, melanotropin (melanocyte-stimulating),
somatotropin,
corticotropin (adrenocorticotropic hormone),
thyrotropin,
follicle-stimulating hormone,
luteinizing hormone (interstitial cell-stimulating hormone),
gonadotropin, prolactin, pepsin
and the like.

Other immunochemicals removable by the method of the invention include a wide variety of drugs, metabolites, virus derived antigens (such as hepatitis B surface antigen), bacterial antigens and derived antibodies (such as syphillis antibodies), parasite derived antigens, allergens and the like.

The method of the invention may be carried out by simply mixing the immunochemical reagents described above, in the blood in the living mammal in-vivo for a sufficient time to have complexes formed between the reagent and the immmunochemical homolog to be removed. Thereafter, the resulting complex may be separated from the blood using conventional techniques such as, for example, filtration and like procedures. An advantage in the method of the invention resides in the lack of toxicity associated with lipid vesicles as a carrier means which can be circulated in-vivo, freely in the blood of a mammal without adverse affect on the blood or the host mammal. Both in vivo and in vitro studies of lipid vesicle's behavior in mammalian blood have demonstrated their lack of toxicity and stability; see for example Gregoriadis, The New England Journal of Medicine, Vol. 295, No. 13, Page 704 (Sept. 23, 1976). The lipid vesicles are eventually removed from circulation in the host mammal, being taken up chiefly in the liver and the spleen where phagocytosis apparently occurs. Thus, even if the lipid vesicle reagents or their reacted complex products are not fully separated from the host mammal's blood as will be described hereinafter; there is little likelihood of an adverse affect on the host mammal.

Those skilled in the art will gain a further appreciation of the invention from a viewing of the accompanying drawing with the following description of a preferred embodiment method of the invention. The accompanying drawing is a schematic block drawing of a system for carrying out the preferred embodiment method. In the drawing, the arrows depict the direction of blood flow.

The apparatus depicted in the drawing is for the extra-corporeal treatment of the blood of a living mammal. The apparatus includes a sterile conduit 12 means for withdrawing the mammal's blood by intravenous catherization and transferring the withdrawn blood to a blood purification unit 14. The blood is passed through the purification unit 14 and then returned to the mammal's blood circulatory system by sterile conduit 16, which comprises an intravenous catheter. The flow of blood from and back to the mammal through the conduits 12, 16 and the purification unit 14 is preferably on a continual flow basis from and back to the mammal. Within the purification unit 14 the blood is pumped by peristaltic pump 18 through an ultrafiltration unit 20 to separate at least part of the blood plasma from the whole blood received from conduit 12. The unseparated blood passes directly into conduit 16 for return to the mammal's circulatory system. The plasma separated during ultrafiltration carries with it the immunologically reactive compound for removal from the mammal's blood. The separated plasma with the compound to be removed is exposed in the ultrafiltration unit 20 to the lipid vesicle bound homolog of the immunologically reactive compound for removal, whereupon immunoreaction occurs to bind the lipid vesicle bound homolog to the compound for removal. The plasma is then filtered through filter 22 to retain the immunological complex, bound to the lipid vesicle, in the unit 20 while the filtrate "plasma" is redirected to the conduit 16 for remixing in the mammal's blood.

The preferred method of the invention employs as the purification unit 20 a unit which comprises an ultrafiltration, semi-permeable membrane, having pore sizes which will permit the passage of blood plasma containing the immunological compound for removal. Ultrafiltration membranes and their method of preparation are widely known. Those skilled in the art are well versed in the manufacture of ultrafiltration membranes having the necessary average pore sizes to selectively separate a wide range of dissolved molecules, including antigens, antibodies and the like. It should be noted here that the term "ultrafiltration" is applied to the process of concentration or removal from the liquid phase, of molecules or aggregates of molecules having dimensions of from about 20 Angstroms to about 20,000 Angstroms. Ultrafiltration and ultrafilter membranes are distinguishable from the process of reverse osmosis or reverse osmosis membranes in that the latter refers to the removal of ions or molecules of dimensions, generally smaller than 20 Angstroms.

Ultrafiltration as practiced in the present invention also differs from conventional dialysis, in that in ultrafiltration the driving force for the separation of water and unwanted materials in the blood is provided by hydraulic pressure, or a pressure differential between surfaces of the ultrafilter membrane. This is in contrast to dialysis separation which occurs by a concentration gradient between the materials on the opposite sides of the membrane.

In the most preferred embodiment method of the invention, the ultrafiltration unit 20 is preferably based upon a bundle of hollow fibers as the separatory membrane. The construction of blood purification units employing hollow fibers is well-known; see for example the apparatus described in U.S. Pat. No. 4,187,180. In the latter patent, apparatus is employed for the dialysis of blood. The same apparatus, modified to include an ultrafilter membrane and without the use of a dialysate may be used. In such an apparatus, the mammalian whole blood is passed through the shell side of the hollow fiber bundle under the pressure provided by pump 18. Circulated countercurrentwise to the passage of the whole blood, within the lumen of each hollow fiber, is a normal saline suspension of the lipid vesicles carrying the immunological homolog of the compound for removal. The lipid vesicles employed preferably have a size of from about 1,000 to about 4,000 Angstrom units so that they may be readily filtered from the saline suspension following reaction of the immunological reagent with the compound for removal. The filter 22 is thus one of sufficient filtration character to remove the lipid vesicle and its bound compounds.

Under the pressure of pump 18, the lipid vesicle reagents do not pass through the ultrafilter membrane to mix with the whole, mammalian blood. However, even if they are not totally removed by filter 22 and do enter the conduit 16 for admixture with the mammalian blood, no adverse affect is anticipated since the reagent is non-toxic to the host mammal as previosuly described.

For the sake of brevity and simplicity, the description of the preferred embodiment method of the invention made above has been limited to a discussion of the essentials required to carry out the method of the invention. It will be appreciated by those skilled in the art that many modifications of the method and the apparatus described above may be made without departing from the spirit and the scope of the invention. For example, the method of the invention may be practiced with apparatus which further includes means of introducing saline solutions to the mammalian blood, pressure monitors, air bubble traps and/or sensors, means of adjusting the water content of the mammalian blood before and after exposure to the lipid vesicle reagents, and like modifications.

The method of the invention is preferably carried out at ambient (room) temperatures and under pressures which are non-damaging to the whole blood components but sufficient to perform ultrafiltration. Exact and optimum pressures may be selected on the basis of trial and error experimentation but is preferably within the range of from about 100 millimeters of mercury to about 180 millimeters of mercury. The pressure may also be selected based upon a desire to withdraw and treat between 15 and 50 millileters per minute of whole blood from the mammal.

Those skilled in the art will appreciate that there are many advantages associated with the method of the invention. For example, since the immunoreactant reagents of the invention are not bound to any fixed support means but are freely circulating vesicles, they can be rapidly removed from contact with the mammal's blood, rapidly exchanged for a different reagent or instantly changed in regard to concentrations etc. employed in the method of the invention. Thus, greater control over the apheresis may be obtained. Also, if a plurality of different immunologically reactive compounds are to be removed, such may be carried out in a single uninterrupted procedure merely by using the appropriate vesicle bound homologs in sequence, without having to change apparatus (only the counter-current circulating immunoreactant vesicle reagent).

What is claimed:

1. A method of removing an immunologically reactive compound from the blood of a living mammal, which comprises;
   removing the whole blood from a living mammal in an extra corporeal, closed circuit;
   separating a portion of the blood plasma from the whole blood within the extra corporeal circuit, by passage of the portion through an ultrafilter, said ultrafilter permitting the passage of plasma with dissolved immunologically reactive compounds, but not permitting the passage of solids within said blood;
   reacting the separated immunologically reactive compound with its homolog bound to the surface of a lipid vesicle;
   separating the resulting lipid vesicle complex from the plasma;
   passing the blood plasma minus lipid vesicle bound immunologically reactive compound to the whole blood in the extra corporeal stream; and
   passing the whole blood back to the mammal's circulatory system.

2. The method of claim 1 wherein the reactive compound is an antigen and the homolog in an antibody.

3. The method of claim 2 wherein the antibody is a monoclonal antibody.

4. The method of claim 1 wherein the reactive compound is an antibody and the homolog is an antigen.

5. The method of claim 1 wherein the lipid vesicles encapsulate a tracer compound.

6. The method of claim 1 wherein the ultrafilter comprises a hollow fiber.

7. The method of claim 1 wherein there are a plurality of different reactive compounds to be removed and a plurality of different homologs are employed, bound to lipid vesicles.

* * * * *